US00PP22756P2

(12) United States Plant Patent
Olesen

(10) Patent No.: US PP22,756 P2
(45) Date of Patent: May 29, 2012

(54) FLORIBUNDA ROSE PLANT NAMED 'POULCAS032'

(50) Latin Name: ***Rosa* hybrid**
Varietal Denomination: Poulcas032

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 12/930,442

(22) Filed: Jan. 7, 2011

(51) Int. Cl.
*A01H 5/00* (2006.01)

(52) U.S. Cl. ..... Plt./151

(58) Field of Classification Search ..... Plt./151
See application file for complete search history.

*Primary Examiner* — Annette Para

(57) ABSTRACT

A new garden rose plant of the floribunda class which has abundant, red flowers and attractive foliage. This new and distinct variety has shown to be uniform and stable in the resulting generations from asexual propagation.

3 Drawing Sheets

Botanical designation: *Rosa* hybrid.
Variety denomination: 'Poulcas032'.

SUMMARY OF THE INVENTION

The present invention constitutes a new and distinct variety of garden rose plant which originated from a controlled crossing between the female seed parent, an unnamed, non-commercial seedling, and the male pollen parent, also an unnamed, non-commercial seedling.

The two parents were crossed during the summer of 2001 and the resulting seeds were planted in a controlled environment in Fredensborg, Denmark. The new variety, named 'Poulcas032', originated as a single seedling from the stated cross.

The new variety may be distinguished from its female seed parent primarily by flower color. The seed parent has pink flowers while the new variety has red flowers.

The new variety may be distinguished from its male pollen parent by flower color. The seed parent has medium red flowers, while the new variety has red flowers.

The objective of the hybridization of this rose variety was to create a new and distinct variety for garden use with unique qualities, such as:

1. Uniform and abundant red flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulcas032' from all other varieties of which we are aware.

As part of the rose development program, Mogens N. Olesen germinated the seeds from the aforementioned hybridization during winter of 2001 and conducted evaluations on the resulting seedlings in a controlled environment in Fredensborg, Denmark. 'Poulcas032' was selected in the spring of 2002 by the inventor as a single plant from the progeny of the aforementioned hybridization.

Asexual reproduction of 'Poulcas032' by traditional budding and rooted cuttings was first done by Mogens N. Olesen in the nursery in Fredensborg, Denmark in July, 2002. This initial and other subsequent asexual propagations conducted in controlled environments have demonstrated that the characteristics of 'Poulcas032' are true to type and are transmitted from one generation to the next.

BRIEF DESCRIPTION OF THE DRAWING

The accompanying color illustrations show as true as is reasonably possible to obtain in color photographs of this type, the typical characteristics of the buds, flowers, leaves, and stems, of 'Poulcas032'. Specifically illustrated in the drawings are.

DETAILED DESCRIPTION OF THE VARIETY

Figure 1:
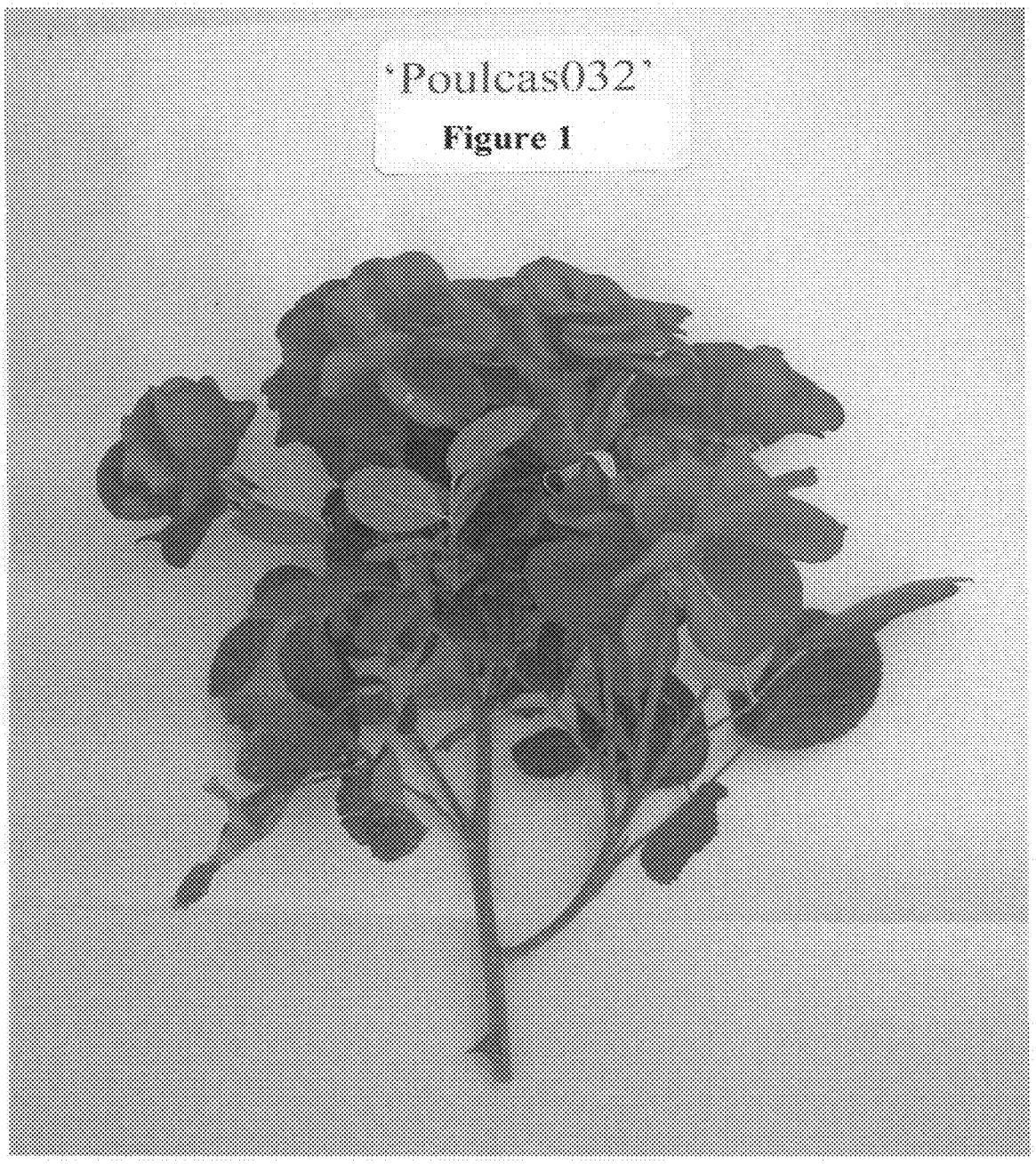
FIG. 1: Cluster of open flowers.
Figure 2:
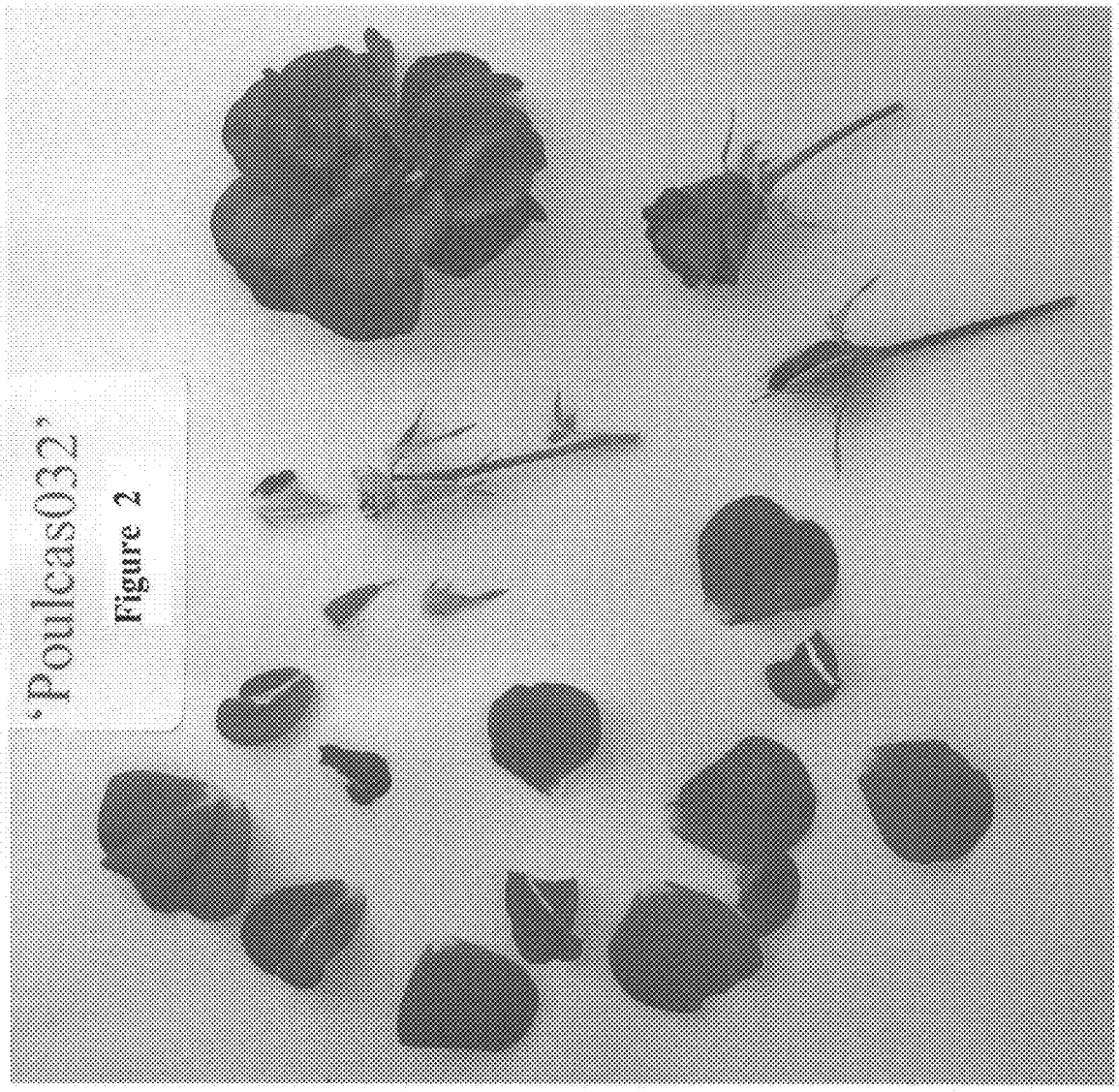
FIG. 2: Open flowers, petals detached, flower bud, and reproductive flower parts.
Figure 3:
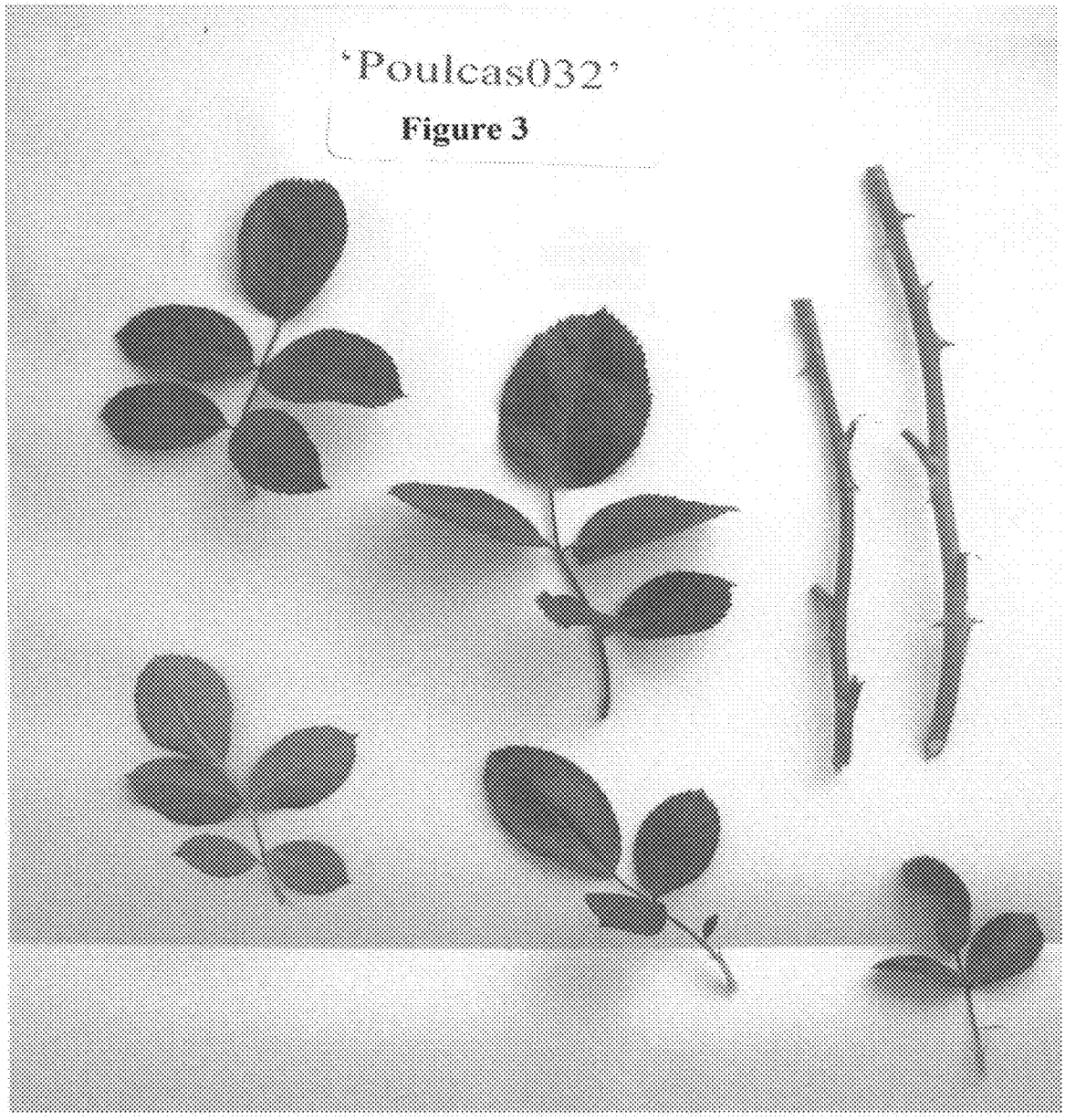
FIG. 3: Leaves and bare stems.

The following is a description of 'Poulcas032', as observed in its growth in in a field nursery in Jackson County, Oreg. Observed plants are 3 years of age, and were grown on *Rosa multiflora* understock. Color references are made using The Royal Horticultural Society (London, England) Colour Chart, 'Poulcas032', except where common terms of color are used.

For a comparison, several physical characteristics of the rose variety 'Poultry', U.S. Plant patent application Ser. No. 10/155,860, now abandoned, are compared to 'Poulcas032' in Chart 1.

CHART 1

| | 'Poulcas032' | 'Poultry' |
|---|---|---|
| Petal Count | 25 to 30 | 70 to 80 |
| Flower Diameter | 60 to 70 | 50 to 80 mm |
| General Tonality of Flower Color | Red Group 53A | Red Group 53A |

FLOWER AND FLOWER BUD

Blooming habit: Continuous.

Flower bud:

*Size*.—Upon opening, 25 mm in length from base of receptacle to end of bud. Bud diameter is 12 mm.

*Bud form*.—Pointed ovoid.

*Bud color*.—As sepals unfold, petals are Red-Purple Group 59A.

*Sepal inner surface*.—Color: Green Group 138C. Surface: Pubescence observed.

*Sepal outer surface*.—Color: Yellow-Green Group 144A. Anthocyanic pigments the color of Greyed-Purple Group 187A observed. Texture: Smooth.

*Sepal shape*.—Apex: Cirrhose. Base: Flat at union with receptacle.

*Sepal margin*.—Margins have medium foliaceous appendages on three of the five sepals.

*Sepal size*.—30 mm long by 7 mm wide.

*Receptacle*.—Texture: Smooth. Shape: Campanulate. Size: 5 mm in height by 6 mm wide. Color: Yellow-Green Group 144A.

*Peduncle*.—Length: 50 to 70 cm. Diameter: 3 to 4 mm. Color: Yellow-Green Group 144A.

*Pedicel*.—Surface: Rough with many small prickles. Length: 50 to 60 mm. Diameter: 2 mm on average. Color: Yellow-Green Group 144C with more than half the surface colored by anthocyanic pigments Greyed-Purple Group N186C. Strength: Strong.

Flower bud development: Flower buds are borne both singly and in clusters of 5 to 7 flower buds per stem.

Flower bloom:

*Fragrance*.—Old rose scent.

*Duration*.—The blooms have a duration on the plant of approximately 10 days. Petals fall cleanly away from plant after flowers have fully matured.

*Size*.—Flower diameter is 60 to 70 mm when open. Flower depth is 25 to 35 mm.

*Flower shape*.—Upon opening general shape is similar to a hybrid tea, high pointed center. After opening, flowers are an open cup with petals curving out from the center. Flowers eventually become loose and open.

*Shape of flower, side view*.—After opening, the upper portion is a flattened convex, while the lower portion is a flattened convex.

Petalage: Under normal conditions, flowers have 25 to 30 petals total, 5 to 8 of which are petaloids.

Petal color: Upon and after opening, outer and inner petals. Upper surface: Red Group 53A. Basal petal spots Yellow Group 4A. Lower surface: Red-Purple Group 60B. Basal petal spots are Yellow Group 4B.

General flower color tonality: On open flower Red Group 53A. No change in the general tonality after the $10^{th}$ day.

Petals:

*Petal reflex*.—Flat.

*Margin*.—Entire with a small point in the center. Weak undulations of margin observed.

*Shape*.—Generally broad elliptic. Apex shape: Rounded. Base shape: Rounded.

*Size*.—35 to 40 mm (l)×60 to 30 mm (w).

*Texture*.—Smooth.

*Thickness*.—Average.

Petaloids:

*Quantity*.—5 to 8.

*Shape*.—Asymmetric.

*Color*.—Upper surface is Red Group 53A. Lower surface is Red-Purple Group 60B. Basal petal spots are Yellow Group 4A (upper) and 4B (lower).

*Size*.—20 to 25.

Reproductive organs:

*Pollen*.—None observed.

*Anthers*.—Size: 2 mm in length. Color: Yellow-Orange Group 16A. Quantity: 50 to 60.

*Filaments*.—Color: Yellow Group 11A. Length: 5 mm.

*Pistils*.—Length: 7 mm. Quantity: 40 on average.

*Stigmas*.—Superior in location relative to the length of the filaments and the height of the anthers. Color: Greyed-Yellow Group 161C.

*Styles*.—Color: Red Group 39B.

*Hips*.—None Observed in the field nursery in Jackson County Oreg.

PLANT

Plant growth: Upright to bushy. When grown as a budded field grown plant on *Rosa multiflora* understock, the average height of the plant is 100 cm and the average width is 90 cm.

Stems:

*Color*.—Juvenile growth: Yellow-Green Group 144A with intonations of Greyed-Orange Group 176A. Mature growth: Yellow-Green Group 144B.

*Length*.—On average, canes are 35 cm from the base of the plant to the flowering portion.

*Diameter*.—5 mm.

*Internodes*.—On mature canes, there is an average distance of 30 mm between nodes.

*Surface texture*.—Young wood: Smooth. Older wood: Smooth.

Prickles:

*Incidence*.—7 prickles per 10 cm of stem.

*Size*.—Average length of prickles on mature stems is 6 mm.

*Shape*.—Linear above a concave lower side.

*Color*.—Juvenile prickles: Yellow-Green Group 144B. Mature prickles: Yellow-Green Group 144B with Greyed-Red Group 179A.

Plant foliage: Normal number of leaflets leaves in middle of the stem: [5, 7] leaflets.

*Compound leaf*.—110 mm (l)×80 (w).

*Quantity*.—3 leaves per 10 cm of stem on average.

*Color of mature foliage*.—Upper side: Yellow-Green Group 147A. Lower side: Yellow-Green Group 147C.

*Color of juvenile foliage*.—Upper side: Yellow-Green Group 146B. Lower side: Yellow-Green Group 146C. Anthocyanin: Greyed-Red Group 181A on the margins.

Plant leaves and leaflets:

*Stipules*.—Size: 20 mm in length. Quantity: 2 per compound leaf. Shape: Linear, slightly broad based with outward extending apecies. Margins: Finely serrated with many stipitate glands. Color: Green Group 143A.

*Petiole*.—Length: 27 mm on average. Diameter: 2 mm.

*Upper surface*.—Color: Yellow-Green Group 146B.

*Lower surface*.—Color: Yellow-Green Group 144B. Observations: Numerous small prickles observed.

*Rachis*.—Length: 40 mm on average.

*Upper surface*.—Color: Yellow-Green Group 146B.

*Lower surface*.—Color: Yellow-Green Group 144B. Observations: Numerous small prickles observed.

*Leaflet*.—Edge: Serrated. Size: Average size of the terminal leaflet on normal leaves is 40 mm in length by 35 mm wide. Shape: Generally orbicular. Base: Rounded. Apex: Obtuse. Texture: Smooth. Thickness: Average. Arrangement: Odd pinnate. Venation: Reticulate. Glossiness: Very Glossy.

Disease resistance: Above average resistance to powdery and downy mildew, rust, black spot, and Botrytis under normal growing conditions in Jackson County, Oreg.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the floribunda rose class named 'Poulcas032', substantially as illustrated and described herein, due to its abundant red flowers, disease resistance, and extended period of bloom.

* * * * *

'Poulcas032'